(12) United States Patent
Koyama

(10) Patent No.: US 10,197,784 B2
(45) Date of Patent: Feb. 5, 2019

(54) OPERATION MECHANISM FOR INSERTION DEVICE AND INSERTION DEVICE

(71) Applicant: OLYMPUS CORPORATION, Tokyo (JP)

(72) Inventor: Reiji Koyama, Tachikawa (JP)

(73) Assignee: OLYMPUS CORPORATION, Tokyo (JP)

( * ) Notice: Subject to any disclaimer, the term of this patent is extended or adjusted under 35 U.S.C. 154(b) by 246 days.

(21) Appl. No.: 15/163,765

(22) Filed: May 25, 2016

(65) Prior Publication Data

US 2016/0266374 A1    Sep. 15, 2016

Related U.S. Application Data

(63) Continuation of application No. PCT/JP2014/080725, filed on Nov. 20, 2014.

(30) Foreign Application Priority Data

Nov. 27, 2013 (JP) .................. 2013-244834

(51) Int. Cl.
*A61B 1/00* (2006.01)
*G02B 23/24* (2006.01)
*A61B 1/005* (2006.01)
*G01N 21/954* (2006.01)

(52) U.S. Cl.
CPC ........ *G02B 23/2476* (2013.01); *A61B 1/0052* (2013.01); *A61B 1/0057* (2013.01); *G01N 21/954* (2013.01); *G01N 2021/9542* (2013.01)

(58) Field of Classification Search
CPC ..... A61B 1/0052; A61B 1/0057; A61B 1/012; A61B 1/00105; G02B 23/2476; G01N 21/954; G01N 2021/9542
See application file for complete search history.

(56) References Cited

U.S. PATENT DOCUMENTS 5,347,993 A * 9/1994 Tanaka ................. A61B 1/0052
600/109

FOREIGN PATENT DOCUMENTS

| EP | 2 478 825 A1 | 7/2012 |
| EP | 2 862 498 A1 | 4/2015 |
| JP | H11-192199 A | 7/1999 |
| JP | 2001-046329 A | 2/2001 |
| WO | 2014/122818 A1 | 8/2014 |

OTHER PUBLICATIONS

Extended Supplementary European Search Report dated Oct. 17, 2017 received in Application No. 14866695.1.
International Search Report dated Feb. 24, 2015 issued in PCT/JP2014/080725.

* cited by examiner

*Primary Examiner* — Timothy J Neal

(74) *Attorney, Agent, or Firm* — Scully, Scott, Murphy & Presser, P.C.

(57) ABSTRACT

An operation mechanism for an insertion device includes a moving section, an operation section configured to operate the moving section, a frame body fixed in the operation section, a long member movable along the frame body according to the operation of the operation section, a first tabular member provided between the frame body and the long member in the operation section, and a plurality of first projecting sections projecting from the first tabular member to the frame body side and disposed in a plurality of holes of the frame body.

14 Claims, 12 Drawing Sheets

H1>H2

H2>H3

OPERATION MECHANISM FOR INSERTION DEVICE AND INSERTION DEVICE

CROSS REFERENCE TO RELATED APPLICATION

This application is a continuation application of PCT/JP2014/080725 filed on Nov. 20, 2014 and claims benefit of Japanese Application No. 2013-244834 filed in Japan on Nov. 27, 2013, the entire contents of which are incorporated herein by this reference.

BACKGROUND OF INVENTION

1. Field of the Invention

The present invention relates to an operation mechanism for an insertion device provided in an operation section and configured to cause a moving section of an insertion section to move and the insertion device.

2. Description of the Related Art

In recent years, insertion devices, for example, endoscopes have been widely used in a medical field and an industrial field.

With the endoscope used in the medical field, by inserting an elongated insertion section into a body cavity, which is a subject, it is possible to observe an organ in the body cavity and perform various kinds of treatment using a treatment instrument inserted into an insert-through channel for the treatment instrument included in the endoscope according to necessity.

With the endoscope used in the industrial field, by inserting an elongated insertion section of the endoscope into an object such as a jet engine or a pipework of a factory, it is possible to perform observation of scratches, corrosion, and the like and inspections of various kinds of treatment and the like of a part to be inspected in the object.

A configuration is well-known in which a moving section, for example, a bending section bendable in a plurality of directions is provided in the insertion section of the endoscope inserted into the subject/object.

The bending section improves progress of the insertion section in a bent section in a conduit and changes an observation direction of an observation optical system provided at a distal end portion located further on a distal end side in an inserting direction (hereinafter simply referred to as distal end side) than the bending section in the insertion section.

Usually, a plurality of bending pieces are coupled along the inserting direction of the insertion section, whereby the bending section provided in the insertion section of the endoscope is configured to be bendable, for example, in upward, downward, left, and right four directions.

Any one of four wires inserted through the insertion section, a distal end in the insertion direction (hereinafter simply referred to as distal end) of which is fixed to the bending piece located on a most distal end side among the bending pieces, is towed by a bending operation device, which is an operation mechanism, provided in the operation section, whereby the bending section is bendable in any one of the upward, downward, left, and right directions.

More specifically, in the bending section, a turning knob for up-down bending operation provided in the operation section is turned, whereby a sprocket for up-down bending, which is a turning body, provided in the operation section is turned via a turning shaft for up-down bending. Thereafter, one of an upper chain part and a lower chain part of a chain member for up-down bending, which is a long member, wound around the sprocket is towed. As a result, one of an upper wire, a proximal end of which in the inserting direction (hereinafter simply referred to as proximal end) is connected to a distal end of the upper chain part via a connection piece and a distal end of which is connected to the bending piece, and a lower wire, a proximal end of which is connected to a distal end of the lower chain part via a connection piece and a distal end of which is connected to the bending piece, is towed, whereby the bending section is bent in the upward direction or the downward direction.

Further, in the bending section, a turning knob for left-right bending operation provided in the operation section is turned, whereby a sprocket for left-right bending, which is a turning body, provided in the operation section is turned via a turning shaft for left-right bending. Thereafter, one of a left chain part and a right chain part of a chain member for left-right bending, which is a long member, wound around the sprocket is towed. As a result, one of a left wire, a proximal end of which is connected to a distal end of the left chain part via a connection piece and a distal end of which is connected to the bending piece, and a right wire, a proximal end of which is connected to a distal end of the right chain part via a connection piece and a distal end of which is connected to the bending piece, is towed, whereby the bending section is bent in the left direction or the right direction.

The turning shaft for left-right bending, to which the sprocket for left-right bending and the turning knob for left-right bending are fixed, is turnably supported by a frame body extending along the inserting direction fixed in the operation section. Note that the turning shaft for up-down bending, to which the turning knob for up-down bending is fixed, covers an outer circumference of the turning shaft for left-right bending.

The frame body is formed in a thin plate shape from a metal member. The frame body functions as a member that performs positioning of various components provided in the operation section and, when a grasping section is fixed to an operation section main body of the operation section, resists a compression force acting on the operation section forward and backward in the inserting direction and functions as a so-called ground plate, on a distal end side of which a proximal end of the insertion section is fixed.

On one surface of the frame body, a guide member cross-shaped in section that separately guides the upper chain part, the lower chain part, the left chain part, and the right chain part forward and backward in the inserting direction not to interfere with one another is also fixed by screws or the like.

Note that, in the guide member, since the guide member is formed in the cross shape in section, four insert-through paths of the respective chain parts are formed. The respective chain sections are inserted through the respective insert-through paths separately from one another, whereby interference among the respective chain parts is prevented by the guide member.

In a state in which the respective chain parts are inserted through the respective insert-through paths, the chain member for up-down bending and the chain member for left-right bending are located to be superimposed along an superimposing direction of the guide member with respect to the frame body.

More specifically, the upper chain part and the left chain part are located to be superimposed and the lower chain part and the right chain part are located to be superimposed. That is, the upper chain part and the lower chain part or the left chain part and the right chain part are in contact with one surface of the frame body.

Since the operation section includes the grasping section grasped by an operator, a reduction in weight of the operation section is desired to make it easy to perform endoscope operation by the operator who grasps the grasping section.

Therefore, Japanese Patent Application Laid-Open Publication No. 11-192199 discloses a configuration in which, a plurality of thinned portions are formed in the metal frame body provided in the operation section, whereby a reduction in weight of the frame body is achieved.

Incidentally, a configuration is also well known in which a plurality of through-holes (hereinafter simply referred to as holes) are formed in the frame body in order to achieve a further reduction in the weight of the operation section.

SUMMARY OF THE INVENTION

An operation mechanism for an insertion device includes: a moving section provided in an insertion section inserted into a subject/object, the moving section being movable; an operation section concatenated to the insertion section in order to operate the moving section; a tabular frame body fixed in the operation section, including a plurality of holes, and configured to position various members disposed in the operation section; a long member movable along the frame body according to the operation of the operation section; a first tabular member provided between the frame body and the long member in the operation section and including a surface that guides the long member; and a plurality of first projecting sections projecting, in the first tabular member, from a surface opposed to the surface that guides the long member to the frame body side and disposed in the plurality of holes.

An insertion device in one aspect of the present invention includes the operation mechanism for the insertion device.

DETAILED DESCRIPTION OF THE PREFERRED EMBODIMENT(S)

Embodiments of the present invention are explained below with reference to the drawings. It should be noted that the drawings are schematic and relations between thicknesses and widths of respective members, ratios of the thicknesses of the respective members, and the like are different from real ones. Naturally, portions where relations and ratios of dimensions are different from one another are included among the drawings.

In the embodiments explained below, an endoscope is explained as an example of an insertion device.

Figure 1:
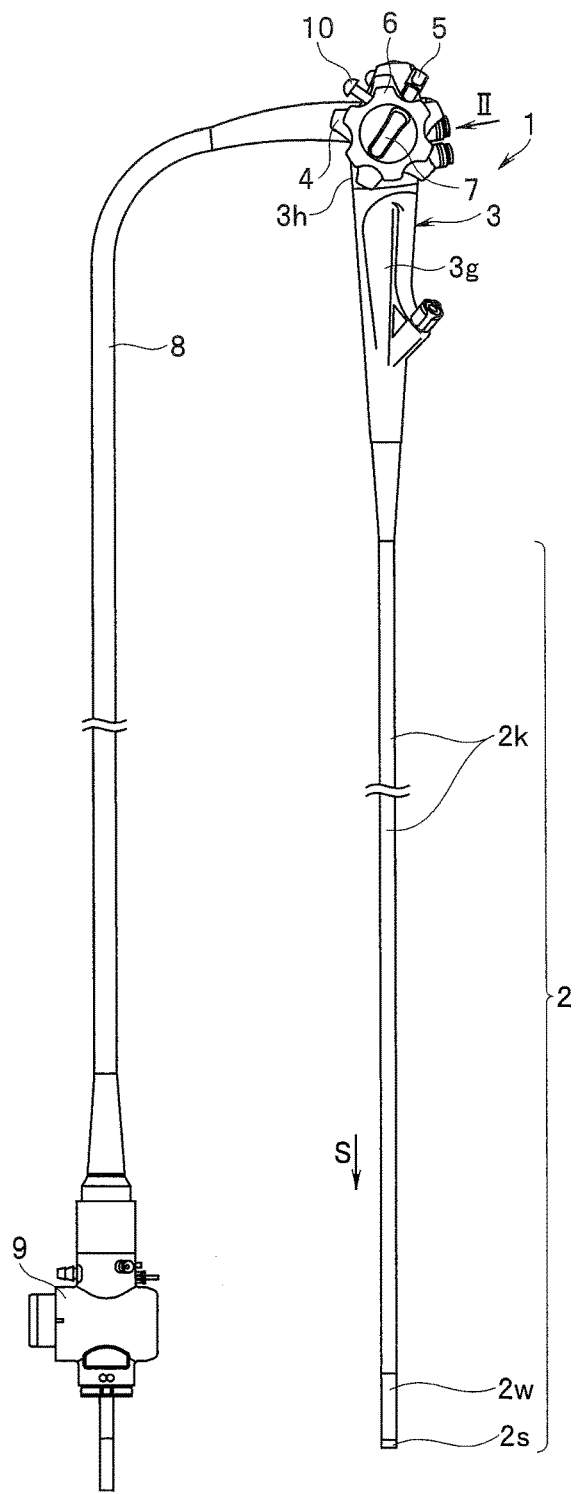
FIG. 1 is a diagram showing an exterior of an endoscope in an embodiment.

FIG. 1 is a diagram showing an exterior of an endoscope in an embodiment.

As shown in FIG. 1, a main part of an endoscope 1 includes an insertion section 2 inserted into a subject/object, an operation section 3 concatenated to a proximal end of the insertion section 2, a universal cord 8 extended from the operation section 3, and a connector 9 provided at an extension end of the universal cord 8. Note that the endoscope 1 is electrically connected to external devices such as a control device and an illumination device via the connector 9.

A main part of the insertion section 2 includes a long flexible tube section 2k extending along an inserting direction S of the insertion section 2, a bending section 2w, which is the moving section, located further in a front of the inserting direction S (hereinafter simply referred to as front) than the flexible tube section 2k, and a distal end portion 2s located further in the front than the bending section 2w.

In the distal end portion 2s, a not-shown image pickup unit that picks up an image of an inside of the subject/object, a now-shown illumination unit that supplies illumination light to the inside of the subject/object, and the like are provided.

The bending section 2w is bendable in, for example, upward, downward, left, and right four directions by turning knobs 4 and 6 for bending operation explained below provided in the operation section 3.

A main part of the operation section 3 includes a grasping section 3g grasped by an operator and an operation section main body 3h connected to a proximal end of the grasping section 3g, the universal cord 8 extending from the operation section main body 3h.

In the operation section main body 3h, the turning knob 4 for up-down bending operation that bends the bending section 2w in an up-down direction and the turning knob 6 for left-right bending operation that bends the bending section 2w in a left-right direction are provided.

In the operation section main body 3h, a fixing lever 5 that fixes a turning position of the turning knob 4, a fixing knob 7 that fixes a turning position of the turning knob 6, and a zoom lever 10 of an image pickup unit provided in the distal end portion 2s are provided.

Note that the turning knob 4, the fixing lever 5, the turning knob 6, and the fixing knob 7 configure a bending operation device 100 (see FIG. 2), which is an operation mechanism for the insertion device explained below in the present embodiment, together with other members explained below provided in the operation section 3.

A configuration of the bending operation device 100 of the endoscope provided in the operation section 3 is explained with reference to FIG. 2 to FIG. 11.

Figure 2:
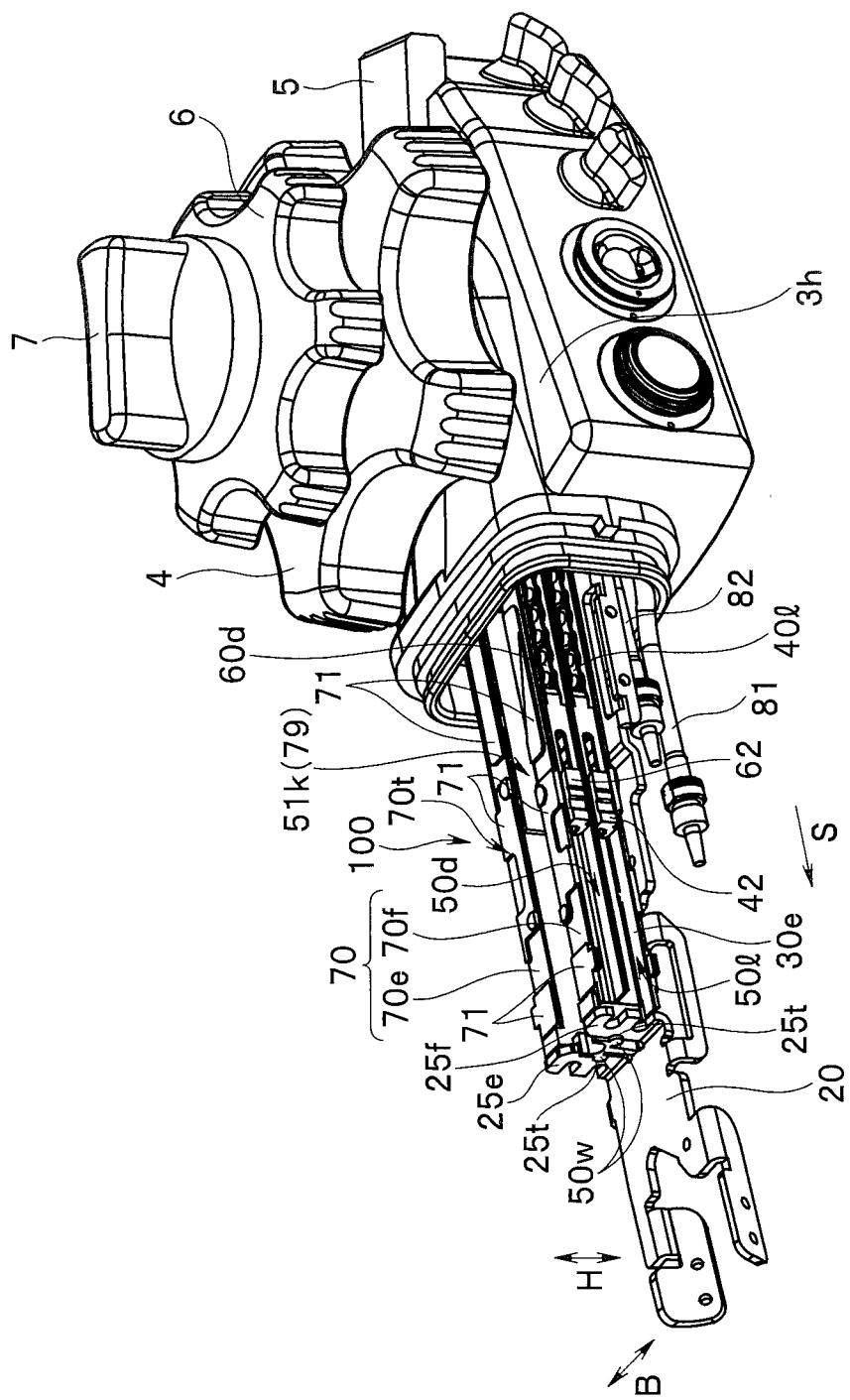
FIG. 2 is a perspective view showing, in an exposed state, together with tubes, a part of a bending operation device in an operation section excluding a grasping section from the operation section of the endoscope viewed from a II direction in FIG. 1.
Figure 3:
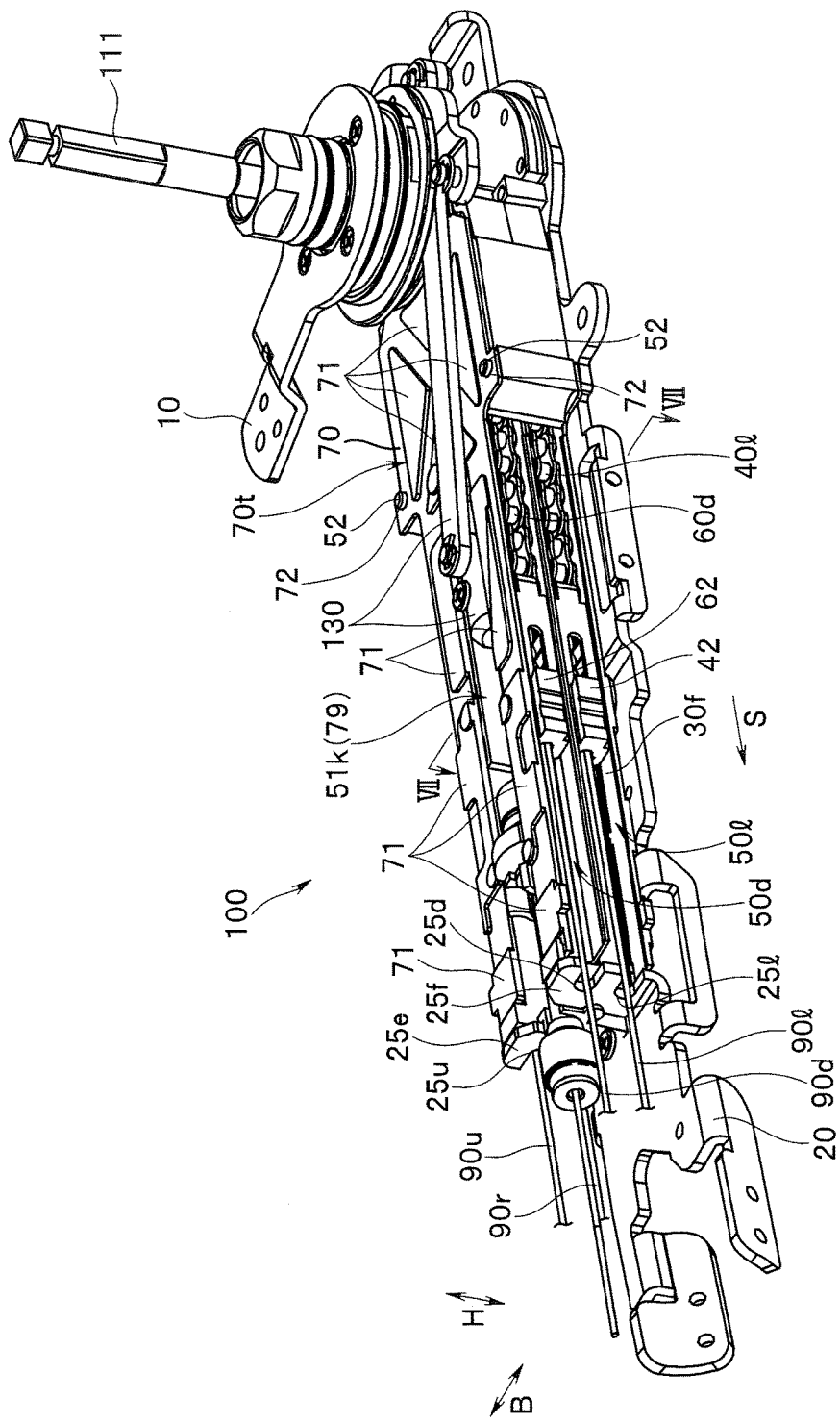
FIG. 3 is a perspective view showing a part of the bending operation device excluding an operation section main body, a turning knob, and a fixing lever from the operation section shown in FIG. 2.

FIG. 2 is a perspective view showing, in an exposed state, together with tubes, a part of the bending operation device in the operation section excluding the grasping section from the operation section of the endoscope viewed from a II direction in FIG. 1. FIG. 3 is a perspective view showing a part of the bending operation device excluding the operation section main body, the turning knob, and the fixing lever from the operation section shown in FIG. 2. Note that, in FIG. 2, wires and a link mechanism of the zoom lever is omitted. In FIG. 3, a turning shaft for up-down bending is omitted.

Figure 4:
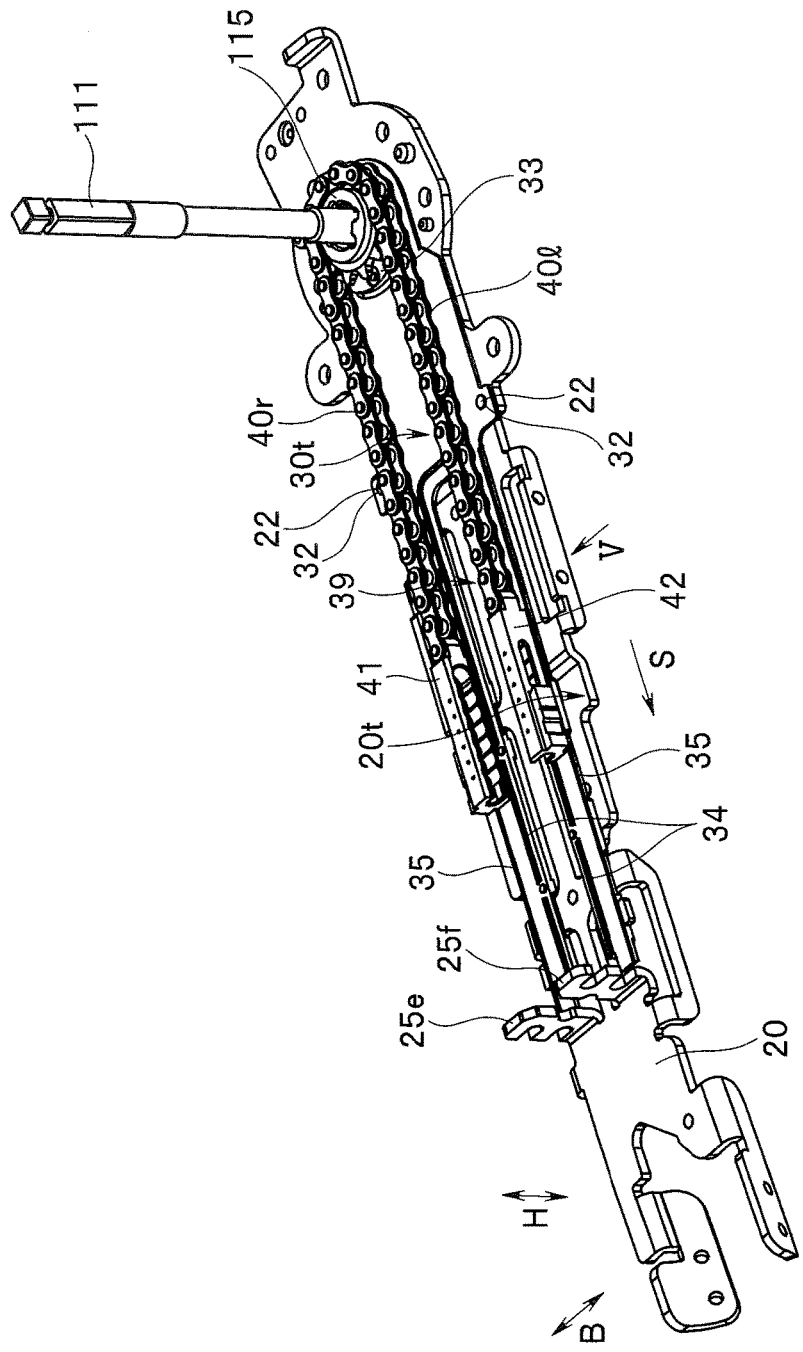
FIG. 4 is a perspective view showing the bending operation device shown in FIG. 3 excluding a chain separator, a second chain cover, a chain member for up-down bending, a zoom lever, and a link mechanism of the zoom lever.
Figure 5:
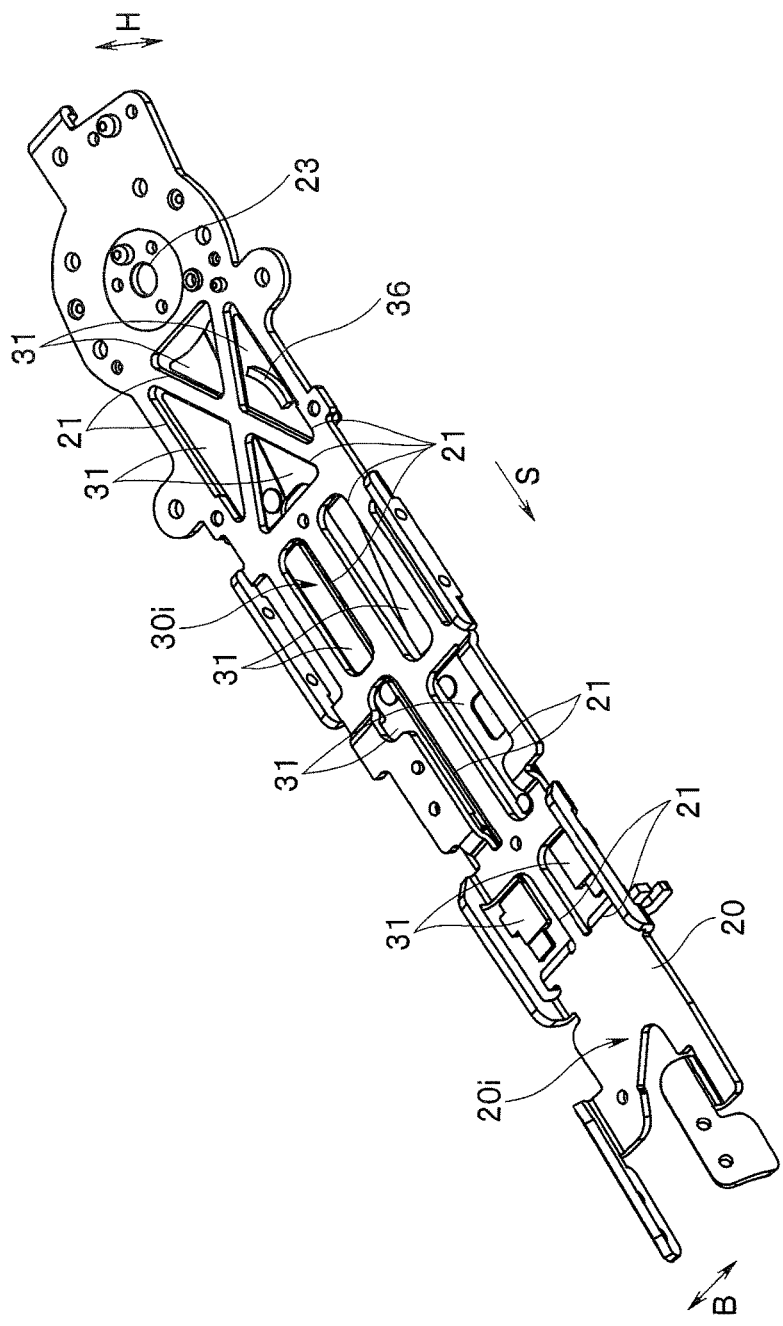
FIG. 5 is a perspective view of a first chain cover and a frame body shown in FIG. 4 viewed from a V direction in FIG. 4.

FIG. 4 is a perspective view showing the bending operation device shown in FIG. 3 excluding a chain separator, a second chain cover, a chain member for up-down bending, the zoom lever, and the link mechanism of the zoom lever. FIG. 5 is a perspective view of a first chain cover and a frame body shown in FIG. 4 viewed from a V direction in FIG. 4. Note that, in FIG. 4, wires are omitted.

Figure 6:
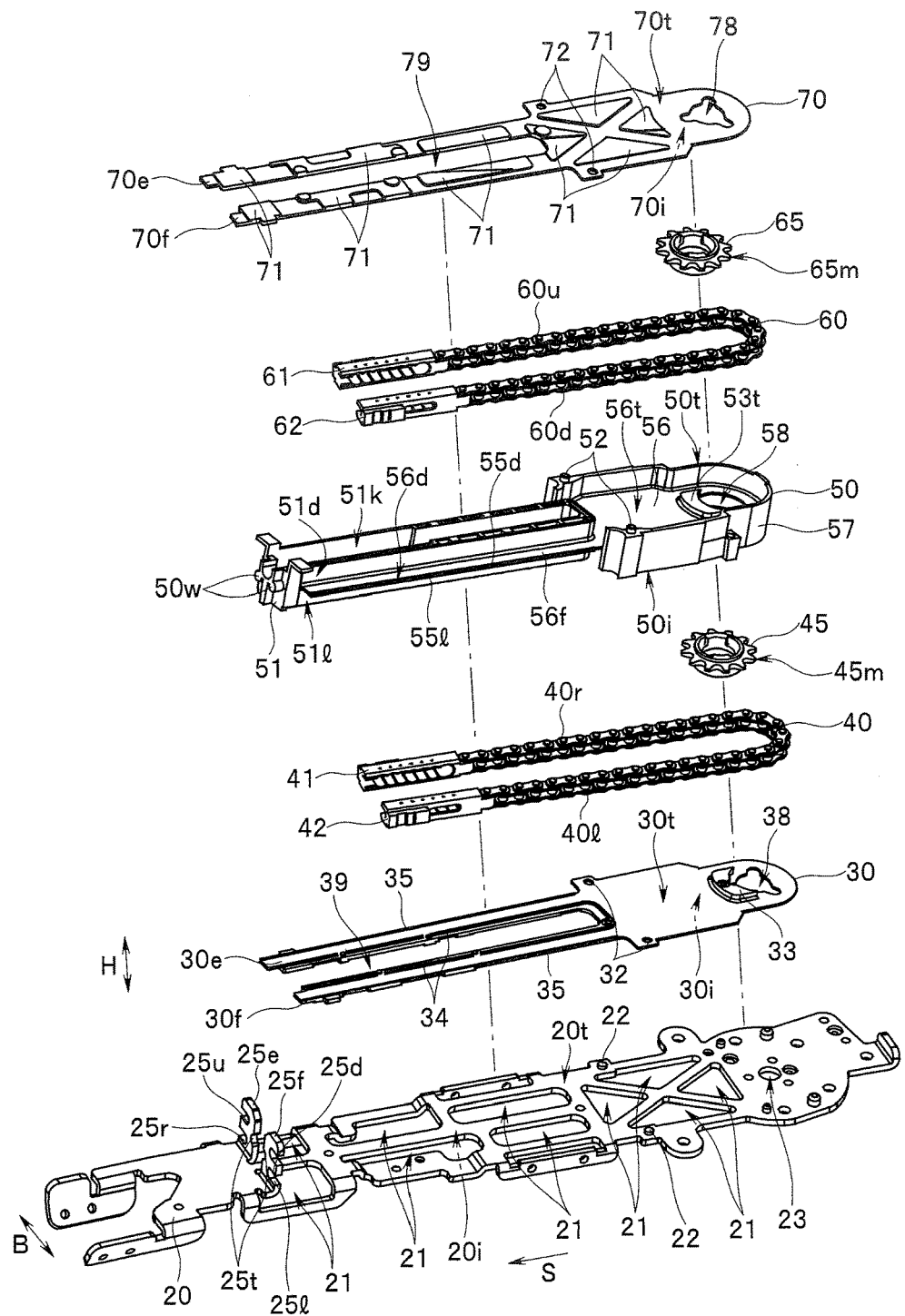
FIG. 6 is an exploded perspective view of a part of the bending operation device shown in FIG. 2.
Figure 7:
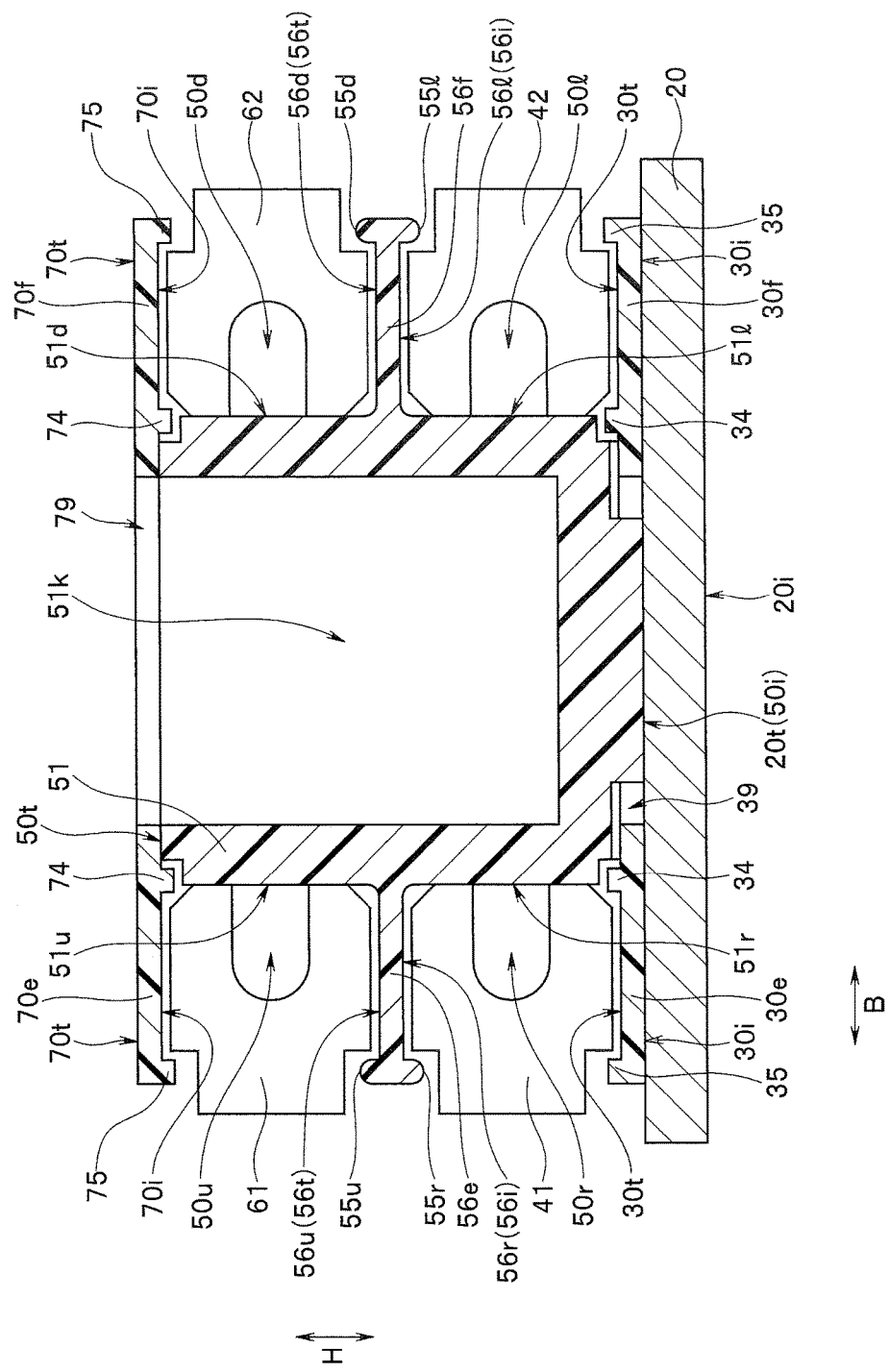
FIG. 7 is a diagram schematically showing, together with respective connection pieces, cross sections of the chain separator, the first chain cover, and the second chain cover taken along a VII-VII line in FIG. 3.

Further, FIG. 6 is an exploded perspective view of a part of the bending operation device shown in FIG. 2. FIG. 7 is a diagram schematically showing, together with respective connection pieces, cross sections of the chain separator, the first chain cover, and the second chain cover taken along a VII-VII line in FIG. 3.

Figure 8:
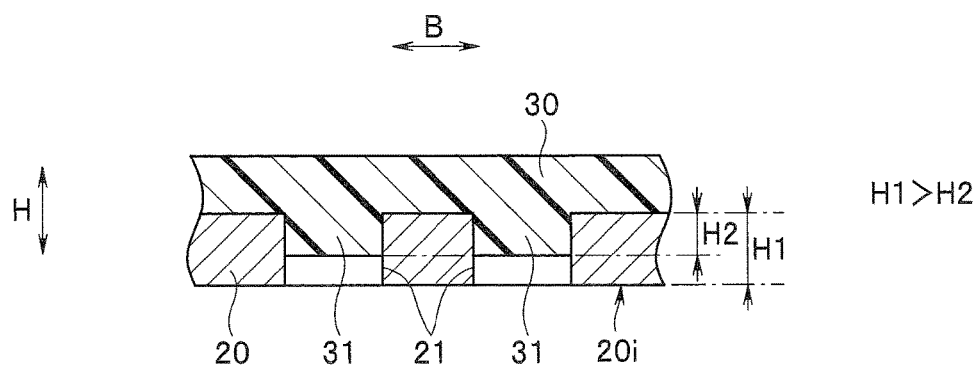
FIG. 8 is a sectional view schematically showing a state in which a plurality of first projecting sections of the first chain cover are fit in a plurality of holes of the frame body shown in FIG. 2.
Figure 9:
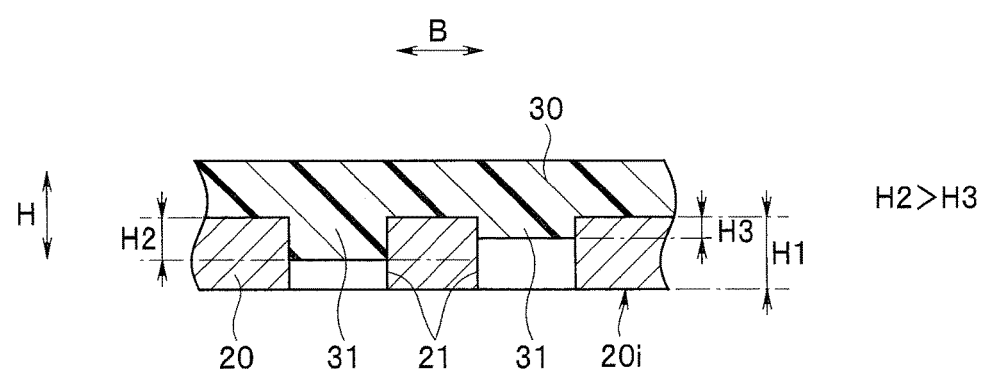
FIG. 9 is a sectional view schematically showing a configuration of a modification in which thickness of the plurality of first projecting sections of the first chain cover shown in FIG. 8 is different for each of the first projecting sections.

FIG. 8 is a sectional view schematically showing a state in which a plurality of first projecting sections of the first chain cover are fit in a plurality of holes of the frame body shown in FIG. 2. FIG. 9 is a sectional view schematically showing a configuration of a modification in which thickness of the plurality of first projecting sections of the first chain cover shown in FIG. 8 is different for each of the first projecting sections.

Figure 10:
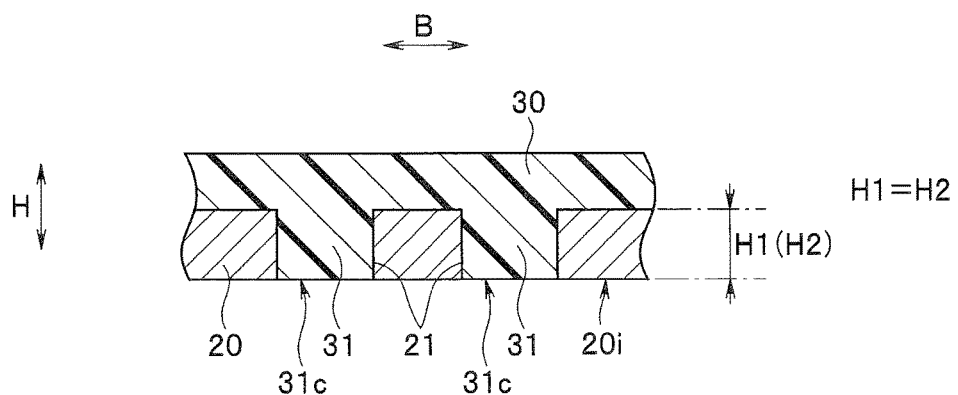
FIG. 10 is a sectional view schematically showing a configuration of a modification in which the thickness of the plurality of first projecting sections of the first chain cover shown in FIG. 8 is the same as thickness of the frame body.
Figure 11:
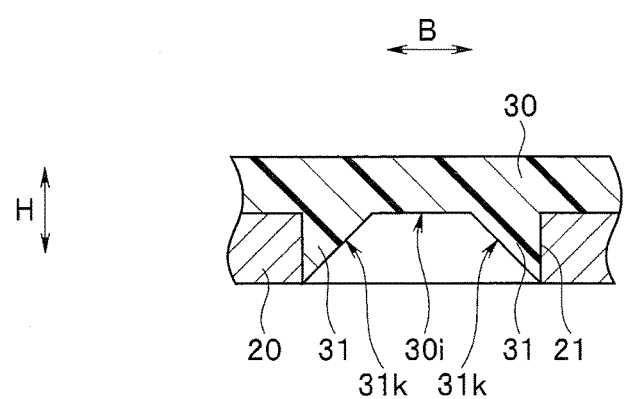
FIG. 11 is a sectional view schematically showing a modification of a shape of the respective first projecting sections shown in FIG. 8 to FIG. 10 in a state in which the first projecting sections are fit in the holes of the frame body.

Further, FIG. 10 is a sectional view schematically showing a configuration of a modification in which the thickness of the plurality of first projecting sections of the first chain cover shown in FIG. 8 is the same as thickness of the frame body. FIG. 11 is a sectional view schematically showing a modification of a shape of the respective first projecting sections shown in FIG. 8 to FIG. 10 in a state in which the first projecting sections are fit in the holes of the frame body.

As shown in FIG. 2 to FIG. 7, the bending operation device 100 includes the turning knobs 4 and 6, the fixing lever 5, and the fixing knob 7 located outside the operation section 3.

The bending operation device 100 includes, in the operation section 3, a not-shown turning shaft for up-down bending, to one end of which the turning knob 4 is fixed, the turning shaft for up-down bending being capable of turning together with the turning knob 4, a sprocket 65 for up-down bending, which is the turning body, fixed to the other end of the turning shaft and capable of turning together with the turning shaft, a turning shaft 111 for left-right bending, to one end of which the turning knob 6 is fixed, the turning shaft 111 for left-right bending being capable of turning together with the turning knob 6, and a sprocket 45 for left-right bending, which is the turning body, fixed to the other end of the turning shaft 111 and capable of turning together with the turning shaft 111.

Further, the bending operation device 100 includes, in the operation section 3, a frame body 20, a first chain cover 30, which is the first tabular member, a chain separator 50, which is a guide member, a second chain cover 70, which is the second tabular member, a chain member for left-right bending 40, which is the long member, wound around the sprocket 45, and a chain member for up-down bending 60, which is the long member, wound around the sprocket 65.

As shown in FIG. 6, the frame body 20 is formed in a thin plate shape from, for example, a metal material to have thickness H1 (see FIG. 8 to FIG. 10) and has a shape in which a part of an end portion extending along the inserting direction S is bent downward in FIG. 6 in a superimposing direction H of the frame body 20 and the chain separator 50.

The frame body 20 extends along the inserting direction S on an inside of the operation section 3 such that a surface 20t explained below of the frame body 20 is opposed to the turning knobs 4 and 6.

In the frame body 20, a plurality of holes 21 piercing through the frame body 20 in the superimposing direction H and a plurality of positioning holes for fixing and positioning various members in the frame body 20 are formed. Note that, since the plurality of holes 21 are formed in the frame body 20, a reduction in weight of the frame body 20 formed from the metal material is achieved.

Further, a distal end side of the frame body 20 is a part to which a proximal end of the insertion section 2 is fixed. On a proximal end side of the frame body 20, a support hole 23 piercing through the frame body 20 in the superimposing direction H for turnably supporting the turning shaft 111 explained below (see FIG. 3 and FIG. 4) is formed.

On a proximal end side of the surface 20t, with which the first chain cover 30 of the frame body 20 comes into contact, for example, two positioning protrusions for positioning the first chain cover 30 are provided to stand from the surface 20t.

Further, on a distal end side of the surface 20t, two supporting members 25e and 25f that hold a distal end of the chain separator 50 are provided to respectively stand from the surface 20t at a predetermined interval in a width direction B orthogonal to the inserting direction S and the superimposing direction H.

In one supporting member 25e of the two supporting members, through-sections 25r and 25u, through which wires 90r and 90u explained below pierce along the inserting direction S, are formed to be superimposed in the superimposing direction H. In the other supporting member 25f of the two supporting members, through-sections 25l and 25d, through which wires 90l and 90d explained below pierce along the inserting direction S, are formed to be superimposed in the superimposing direction H.

On respective opposed surfaces in the width direction B of the respective supporting members 25e and 25f, locking grooves 25*t*, in which locking sections 50*w* (see FIG. 2) explained below provided at the distal end of the chain separator 50 are respectively locked, are formed.

The first chain cover 30 is formed in a thin plate shape from resin having high lubricity such as polyacetar (POM) and is located to be sandwiched between the frame body 20 and the chain separator 50 in the superimposing direction H.

Two positioning holes 32 formed to pierce through the first chain cover 30 in the superimposing direction H are fit in two positioning protrusions 22 of the frame body 20, whereby the first chain cover 30 is positioned with respect to the frame body 20.

In the first chain cover 30, a slit 39 is formed along the inserting direction S in a center in the width direction B of a front half section in the inserting direction S, whereby the front half section is formed to be forked. Note that, in the following explanation, one side in the width direction B of the front half section of the first chain cover 30 is referred to as one side 30*e* and the other side is referred to as the other side 30*f*.

Further, as shown in FIG. 5, a first surface 30*i* on the frame body 20 side of the first chain cover 30 is a surface in contact with the surface 20*t* of the frame body 20. On the first surface 30*i*, projecting sections 31, which are a plurality of first projecting sections, projecting to the frame body 20 side from the first surface 30*i* and fitting in the plurality of holes 21 of the frame body 20 are formed.

Note that, in the present embodiment, as shown in FIGS. 5 and 8, thickness H2 of the plurality of projecting sections 31 is formed smaller than thickness H1 of the frame body (H1>H2).

The plurality of projecting sections 31 close the plurality of holes 21 by fitting in the plurality of holes 21. Consequently, when various members such as tubes 81 and 82 shown in FIG. 2, a cylinder to which the tubes 81 and 82 are connected, a pipe sleeve that couples intermediate positions of the tubes, signal lines, a light guide, and an earth terminal (none of which are shown in the figure) are assembled in the operation section 3, the various members in the operation section 3 in contact with the surface 20*i* opposed to the surface 20*t* of the frame body 20 are prevented from being caught by the plurality of holes 21.

Note that, as shown in FIG. 9, thickness of the plurality of projecting sections 31 may be different for each of the plurality of projecting sections 31 (H2>H3). This is because, since sizes of the various members in the operation section 3 in contact with the surface 20*i* and in contact with top surfaces 31*c* of the respective projecting sections 31 are not fixed, if the thickness of the projecting sections 31 is varied for each of the sizes of the various members in contact with the top surfaces 31*c*, the various members in the operation section 3 are less likely to be caught by the plurality of holes 21.

Further, as shown in FIG. 10, in a state in which the thickness H2 of the plurality of projecting sections 31 is formed the same as the thickness H1 of the frame body 20 (H2=H1) and the plurality of projecting sections 31 are fit in the plurality of holes 21, the thickness of the respective projecting sections 31 may be defined such that the top surfaces 31*c* of the respective projecting sections 31 are flush with the surface 20*i* of the frame body.

Consequently, the various members in the operation section 3 cannot be fit in the plurality of holes 21. Therefore, it is possible to surely prevent the various members in the operation section 3 from being caught by the plurality of holes 21.

The plurality of projecting sections 31 may have different shapes for each of the plurality of projecting sections 31. This is because, since shapes of the various members in the operation section 3 in contact with the surface 20*i* and the top surfaces 31*c* are not fixed, if the shape of the projecting sections 31 is varied for each of the shapes of the various members in contact with the top surfaces 31*c*, the various members in the operation section 3 are less easily caught by the plurality of holes 21.

Therefore, if the shape of the plurality of projecting sections 31 is formed the same as the shape of the plurality of holes 21, it is possible to more surely prevent the various members in the operation section 3 from being caught by the plurality of holes 21.

Further, if the shape of the plurality of projecting sections 31 is formed in the shape same as the shape of the plurality of holes 21 and, as shown in FIG. 10, the thickness H2 of the plurality of projecting sections 31 is formed the same as the thickness H1 of the frame body 20, since there is no level difference in the plurality holes 21, it is possible to surely prevent the various members in the operation section 3 from being caught by the plurality of holes 21.

As shown in FIG. 11, the plurality of projecting sections 31 may be formed in a shape in which only a circumferential edge portion projects to the frame body 20 side from the first surface 30*i* and a surface between the circumferential edge portion and the first surface 30*i* is an inclined surface 31*k*.

Consequently, since there is no level difference in the plurality of holes 21, it is possible to surely prevent, with the inclined surface 31*k*, the various members in the operation section 3 from being caught by the plurality of holes 21.

As shown in FIG. 5, a guide projecting section 36, which is the second projecting section, fit in the plurality of holes 21 and configured to guide disposition of the various members in the operation section 3 is provided in at least a part of the plurality of projecting sections 31.

More specifically, the guide projecting section 36 defines, for example, a traveling direction in the operation section 3 of the tube 82 and guides the tube 82 to prevent a situation in which the tube 82 is caught by a level difference of an inner wall of the operation section main body 3*h* and the tube 82 is less easily assembled or the tube 82 is buckled.

Naturally, the guide projecting section 36 is not limited to the guide of the tube 82 and may have a function of restricting a traveling state of other various members provided in the operation section 3 and preventing the various members from being caught. A plurality of guide projecting sections 36 may be provided.

Note that the guide projecting section 36 may be formed on the first surface 30*i* of the first chain cover 30.

As shown in FIG. 6, on a proximal end side of the first chain cover 30, a holding hole 38 for the sprocket 45 piercing through the first chain cover 30 in the superimposing direction H is formed. The sprocket 45 is turnably held in the holding hole 38 such that a winding section 45*m* is exposed to the second surface 30*t* side.

The second surface 30*t* opposed to the first surface 30*i* of the first chain cover 30 configures a surface that guides the chain member for left-right bending 40.

More specifically, the chain member for left-right bending configures a chain member, which is the second long member, wound around the winding section 45*m*. An intermediate position of the chain member for left-right bending 40 is wound around the winding section 45*m*, whereby the chain member for left-right bending 40 is formed in a U shape while including a one side 40*r* and the other side 40*l*.

Note that the chain member for left-right bending 40 is not limited to the chain member for left-right bending configured only by the chain member and may be a chain member for left-right bending combined with, for example, a chain member including a wire having strength in a pulling direction.

As shown in FIG. 3, a proximal end of the wire 90r, which is the first wire for right bending, functioning as a long member, a distal end of which is fixed to a distal end of the bending section 2w, is connected to a distal end of the one side 40r via a connection piece 41, which is the first connection piece.

A proximal end of the wire 90l, which is the second wire for left bending functioning as a long member, a distal end of which is fixed to the distal end of the bending section 2w, is connected to a distal end of the other side 40l via a connection piece 42, which is the second connection piece.

Note that the wire 90r pierces through the through-section 25r of the supporting member 25e along the inserting direction S. The wire 90l pierces through the through-section 25l of the supporting member 25f along the inserting direction S.

That is, in the insertion section 2 and the operation section 3, an intermediate position of the chain member for left-right bending 40 is wound around the winding section 45m, whereby the long member is provided in a U shape while including the wire 90r and the one side 40r, which are one side of the long member, and the wire 90l and the other side 40l, which are the other side of the long member.

Consequently, when the turning knob 6 is turned, the sprocket 45 turns via the turning shaft 111, the wire 90r and the one side 40r are towed, and the wire 90l and the other side 40l are loosened, the bending section 2w bends in the right direction. When the wire 90r and the one side 40r are loosened and the wire 90l and the other side 40l are towed, the bending section 2w bends in the left direction.

At this point, the chain member for left-right bending 40 is slidable with respect to the second surface 30t of the first chain cover 30. Consequently, the chain member for left-right bending 40 is prevented from being caught by the plurality of holes 21 of the frame body 20.

Note that, on the second surface 30t of the one side 30e of the first chain cover 30, the one side 40r of the chain member for left-right bending 40 is slidable forward and backward in the inserting direction S in an insert-through path 50r (see FIG. 7) explained below.

On the second surface 30t of the other side 30f, the other side 40l of the chain member for left-right bending 40 is slidable forward and backward in the inserting direction S in an insert-through path 50l (see FIG. 7) explained below.

Note that, as explained below, the second surface 30t of the one side 30e is exposed to the insert-through path 50r. The second surface 30t of the other side 30f is exposed to the insert-through path 50l.

As shown in FIG. 4, FIG. 6, and FIG. 7, on the second surface 30t of the one side 30e and the other side 30f of the first chain cover 30, ribs 34 and 35, which are the third projecting section, are formed along the inserting direction S at an end portion parallel to the inserting direction S, more specifically, an end portion surrounding the slit 39 and an end portion on an outer side in the width direction B.

The rib 34 is formed in a C shape. The rib 34 guides the one side 40r of the chain member for left-right bending 40 not to come off to the slit 39 side from the second surface 30t of the one side 30e and guides the other side 40l of the chain member for left-right bending 40 forward and backward in the inserting direction S not to come off to the slit 39 side from the second surface 30t of the other side 30f.

The rib 35 guides the one side 40r of the chain member for left-right bending 40 not to come off to the outer side in the width direction B from the second surface 30t of the one side 30e and guides the other side 40l of the chain member for left-right bending 40 forward and backward in the inserting direction S not to come off to the outer side in the width direction B from the second surface 30t of the other side 30f.

That is, the ribs 34 and 35 guide the one side 40r and the other side 40l, more specifically, at least the connection piece 41 and the connection piece 42 forward and backward in the inserting direction S not to come off the respective insert-through paths 50r and 50l.

On the second surface 30t of the first chain cover 30, in a front and a vicinity of the holding hole 38, a projecting section for alignment 33, which is the fourth projecting section, is provided. The projecting section for alignment 33 guides the one side 40r of the chain member for left-right bending 40 to the insert-through path 50r, that is, the second surface 30t of the one side 30e of the first chain cover 30, guides the other side 40l of the chain member for left-right bending 40 to the insert-through path 50l, that is, the second surface 30t of the other side 30f of the first chain cover 30, and prevents the one side 40r and the other side 40l from interfering with each other because of loosening of one of the one side 40r and the other side 40l.

Note that, as explained above, the first chain cover 30 has the different shapes on the first surface 30i and the second surface 30t. Therefore, in assembly, the operator does not mistake an attaching direction of the first chain cover 30.

The second chain cover 70 is formed in a thin plate shape from resin having high lubricity such as polyacetar (POM) and is in contact with and located on a surface 50t on an opposite side of the frame body 20 of the chain separator 50 in the superimposing direction H.

Two positioning holes 72 formed to pierce through the second chain cover 70 in the superimposing direction H are fit in two positioning protrusions 52 formed on the surface 50t of the chain separator 50, whereby the second chain cover 70 is positioned with respect to the chain separator 50.

In the second chain cover 70, a slit 79 is formed along the inserting direction S in a center in the width direction B of a front half section in the inserting direction S, whereby the front half section is formed to be forked. Note that, in the following explanation, one side in the width direction B of the front half section of the second chain cover 70 is referred to as one side 70e and the other side is referred to as the other side 70f.

Further, as shown in FIG. 3, a first surface 70t on an opposite side of the second chain cover 70 and the chain separator 50 is a surface to which a link mechanism 130 of the zoom lever 10 is opposed. On the first surface 70t, projecting sections 71, which are the plurality of first projecting sections, projecting to the link mechanism 130 side from the first surface 70t are formed. Note that the respective projecting sections 71 are formed in thickness and a shape that do not hinder driving of the link mechanism 130.

On a proximal end side of the second chain cover 70, a holding hole 78 for the sprocket 65 piercing through the second chain cover 70 in the superimposing direction H is formed. The sprocket 65 is turnably held in the holding hole 78 such that a winding section 65m is exposed to a second surface 70i side explained below.

The second surface 70i opposed to the first surface 70t of the second chain cover 70 configures a surface that guides the chain member for up-down bending 60.

More specifically, the chain member for up-down bending 60 configures a chain member, which is the second long member, wound around the winding section 65m. An intermediate position of the chain member for up-down bending 60 is wound around the winding section 65m, whereby the chain member for up-down bending 60 is formed in a U shape while including one side 60u and the other side 60t.

Note that the chain member for up-down bending 60 is not limited to the chain member for up-down bending configured only by the chain member and may be a chain member for up-down bending combined with, for example, a chain member including a wire having strength in a pulling direction.

As shown in FIG. 3, a proximal end of the wire 90u, which is the first wire for upper bending, functioning as a long member, a distal end of which is fixed to the distal end of the bending section 2w, is connected to a distal end of the one side 60u via a connection piece 61, which is the first connection piece.

A proximal end of the wire 90d, which is the second wire for downward bending functioning as a long member, a distal end of which is fixed to the distal end of the bending section 2w, is connected to a distal end of the other side 60d via a connection piece 62, which is the second connection piece.

Note that the wire 90u pierces through the through-section 25u of the supporting member 25e along the inserting direction S. The wire 90d pierces through the through-section 25d of the supporting member 25f along the inserting direction S.

That is, in the insertion section 2 and the operation section 3, an intermediate position of the chain member for up-down bending 60 is wound around the winding section 65m, whereby the long member is provided in a U shape while including the wire 90u and the one side 60u, which are one side of the long member, and the wire 90d and the other side 60d, which are the other side of the long member.

Consequently, when the turning knob 4 is turned, the sprocket 65 turns via the not-shown turning shaft, the wire 90u and the one side 60u are towed, and the wire 90d and the other side 60d are loosened, the bending section 2w bends in the upward direction. When the wire 90u and the one side 60u are loosened and the wire 90d and the other side 60d are towed, the bending section 2w bends in the downward direction.

At this point, the chain member for up-down bending 60 is slidable with respect to the second surface 70i of the second chain cover 70.

Note that, on the second surface 70i of the one side 70e of the second chain cover 70, the one side 60u of the chain member for up-down bending 60 is slidable forward and backward in the inserting direction S in an insert-through path 50u (see FIG. 7) explained below.

On the second surface 70i of the other side 70f, the other side 60d of the chain member for up-down bending 60 is slidable forward and backward in the inserting direction S in an insert-through path 50d (see FIG. 7) explained below.

Note that, as explained below, the second surface 70i of the one side 70e is exposed to the insert-through path 50u. The second surface 70i of the other side 70f is exposed to the insert-through path 50d.

As shown in FIG. 7, on the second surface 70i of the one side 70e and the other side 70f of the second chain cover 70, ribs 74 and 75, which are the sixth projecting section, are formed along the inserting direction S at an end portion parallel to the inserting direction S, more specifically, an end portion surrounding the slit 79 and an end portion on the outer side in the width direction B.

The rib 74 is formed in a C shape. The rib 74 guides the one side 60u of the chain member for up-down bending 60 not to come off to the slit 79 side from the second surface 70i of the one side 70e and guides the other side 60d of the chain member for up-down bending 60 forward and backward in the inserting direction S not to come off to the slit 79 side from the second surface 70i of the other side 70f.

The rib 75 guides the one side 60u of the chain member for up-down bending 60 not to come off to the outer side in the width direction B from the second surface 70i of the one side 70e and guides the other side 60d of the chain member for up-down bending 60 forward and backward in the inserting direction S not to come off to the outer side in the width direction B from the second surface 70i of the other side 70f.

That is, the ribs 74 and 75 guide the one side 60u and the other side 60d, more specifically, at least the connection piece 61 and the connection piece 62 forward and backward in the inserting direction S not to come off the respective insert-through paths 50u and 50d.

On the second surface 70i of the second chain cover 70, in a front and a vicinity of the holding hole 78, a not-shown projecting section for alignment, which is the seventh projecting section, is provided. The projecting section for alignment guides the one side 60u of the chain member for up-down bending 60 to the insert-through path 50u, that is, the second surface 70i of the one side 70e of the second chain cover 70, guides the other side 60d of the chain member for up-down bending 60 to the insert-through path 50d, that is, the second surface 70i of the other side 70f of the second chain cover 70, and prevents the one side 60u and the other side 60d from interfering with each other because of loosening of one of the one side 60u and the other side 60d.

Note that, as explained above, the second chain cover 70 has the different shapes on the first surface 70t and the second surface 70i. Therefore, in assembly, the operator does not mistake an attaching direction of the second chain cover 70.

The first chain cover 30 and the second chain cover 70 may be formed to have the same shape. That is, the first chain cover 30 and the second chain cover 70 may be configured as the same member.

That is, the one side 30e, the other side 30f, the plurality of projecting sections 31, the positioning holes 32, the ribs 34 and 35, the projecting section for alignment 33, and the holding hole 38 of the first chain cover 30 are respectively equivalent to the other side 70f, the one side 70e, the plurality of projecting sections 71, the positioning holes 72, the ribs 74 and 75, the not-shown projecting section for alignment, and the holding hole 78 of the second chain cover 70.

The first surface 30i of the first chain cover 30 is equivalent to the first surface 70t of the second chain cover 70. The second surface 30t is equivalent to the second surface 70i. Note that, in this case, the guide projecting section 36 is provided in the first surface 70t or the projecting section 71 of the second chain cover 70 as well.

That is, the first chain cover 30 may be disposed such that the first surface 30i is in contact with the surface 50t of the chain separator 50. Further, the second chain cover 70 may be disposed between the chain separator 50 and the frame body 20 in the superimposing direction H such that the first surface 70*t* is directed to the frame body 20 side and the second surface 70*i* is directed to the chain separator 50 side. In this case, the plurality of projecting sections 71 are fit in the plurality of holes 21.

Note that, when the first chain cover 30 is used instead of the second chain cover 70, that is, when the chain separator 50 is sandwiched between the first chain covers 30 in the superimposing direction H, the thickness and the shape of the plurality of projecting sections 31 need to be the thickness and the shape that prevent the various members in the operation section 3 from being caught by the plurality of holes of the frame body 20 as explained above and, besides, need to be thickness and a shape that do not hinder driving of the link mechanism 130. In this case, the respective first chain covers 30 are axially symmetrical in the superimposing direction H with respect to a center of the chain separator 50.

The same applies when the second chain cover 70 is used instead of the first chain cover 30, that is, when the chain separator 50 is sandwiched between the second chain covers 70 in the superimposing direction H. In this case, the respective second chain covers 70 are axially symmetrical in the superimposing direction H with respect to the center of the chain separator 50.

On the surface 20*t* of the frame body 20, the chain separator 50 that guides movement of the chain member for left-right bending 40 and the chain member for up-down bending 60 forward and backward in the inserting direction S in the operation section 3 is fixed to sandwich the first chain cover 30 between the surface 20*t* and the chain separator 50.

The chain separator 50 is formed from resin having high lubricity and elasticity such as polyacetar (POM). As shown in FIG. 6 and FIG. 7, the chain separator 50 includes a columnar section 51, a thin plate-like part 56, and a wall section 57.

Note that the columnar section 51, the thin plate-like part 56, and the wall section 57 are integrally formed. Portions having high elasticity in the chain separator 50 may be only portions of thin plate-like parts 56*e* and 56*f* explained below and ribs 55*u*, 55*d*, 55*r*, and 55*l* explained below.

On the surface 50*t* on the second chain cover 70 side of the chain separator 50, the positioning protrusions 52, in which the positioning holes 72 of the second chain cover 70 are fit, are formed.

Like the first chain cover 30 and the second chain cover 70, a front half section in the inserting direction S of the thin plate-like part 56 is formed to be forked. One side 56*e* and the other side 56*f* in the width direction B are fixed to centers in the superimposing direction H on both side surfaces in the width direction B of the columnar section 51 along the inserting direction S.

Note that a surface 56*i* on the first chain cover 30 side of the thin plate-like part 56 is opposed to the second surface 30*t* of the first chain cover 30. A surface 56*t* on the second chain cover 70 side of the thin plate-like part 56 is opposed to the second surface 70*i* of the second chain cover 70.

To cover an outer circumferential end portion excluding the surface 56*i* and the surface 56*t* on a proximal end side of the thin plate-like part 56, a center in the superimposing direction H of the wall section 57 is fixed to the outer circumferential end portion.

An end portion on the surface 50*i* side of the wall section 57 is a surface in contact with the surface 20*t* of the frame body 20. An end portion on the surface 50*t* side is a surface in contact with the second surface 70*i* of the second chain cover 70.

Note that the wall section 57 has a function of preventing the chain member for left-right bending 40 wound around the winding section 45*m* of the sprocket 45 from coming off to an outside of the chain separator 50 from a proximal end side of the surface 56*i* of the thin plate-like part 56 and preventing the chain member for up-down bending 60 wound around the winding section 65*m* of the sprocket 65 from coming off to the outside of the chain separator 50 from a proximal end side of the surface 56*t* of the thin plate-like part 56.

A holding hole 58 for the sprockets 45 and 65 piercing through the thin plate-like part 56 in the superimposing direction H is formed on the proximal end side of the thin plate-like part 56. The sprocket 45 is fit in the holding hole 58 and the holding hole 38, whereby the sprocket 45 is turnably held on the surface 56*i* side of the thin plate-like part 56. The sprocket 65 is fit in the holding hole 58 and the holding hole 78, whereby the sprocket 65 is turnably held on the surface 56*t* side of the thin plate-like part 56.

On the surface 56*i* of the thin plate-like part, in a front and a vicinity of the holding hole 58, a not-shown projecting section for alignment is provided. The projecting section for alignment guides the one side 40*r* of the chain member for left-right bending 40 to the insert-through path 50*r* explained below, guides the other side 40*l* of the chain member for left-right bending 40 to the insert-through path 50*l* explained below, and preventing, in conjunction with the projecting section for alignment 33 of the first chain cover 30, the one side 40*r* and the other side 40*l* from interfering with each other because of loosening of one of the one side 40*r* and the other side 40*l*.

Further, on the surface 56*t* of the thin plate-like part, in a front and a vicinity of the holding hole 58, a projecting section for alignment 53*t* is provided. The projecting section for alignment 53*t* guides the one side 60*u* of the chain member for up-down bending 60 to the insert-through path 50*u* explained below, guides the other side 60*d* of the chain member for up-down bending 60 to the insert-through path 50*d* explained below, and prevents, in conjunction with the projecting section for alignment of the second chain cover 70, the one side 60*u* and the other side 60*d* from interfering with each other because of loosening of one of the one side 60*u* and the other side 60*d*.

The columnar section 51 includes, on an inside, a space 51*k* opening upward in the superimposing direction H in FIG. 6 and FIG. 7. In the space 51*k*, as shown in FIG. 3, the link mechanism 130 is fit via the slit 79 of the second chain cover 70.

The columnar section 51 is set in contact with the surface 20*t* of the frame body 20 via the slit 39 of the first chain cover 30.

The locking sections 50*w* projecting forward are formed at a distal end of the columnar section 51. The locking sections 50*w* are locked to the respective locking grooves 25*t* of the two supporting members 25*e* and 25*f* standing from the surface 20*t* of the frame body 20. In a state in which the locking sections 50*w* are locked to the locking grooves 25*t* and the distal end of the chain separator 50 is positioned, the chain separator 50 is fixed to the surface 20*t* by screws or the like.

As shown in FIG. 7, the insert-through path 50*r*, which is the first insert-through path through which the one side 40*r* and the connection piece 41 of the chain member for left-right bending 40 are inserted, is formed in the chain separator 50 by, in conjunction with the second surface 30*t* of the one side 30*e* of the first chain cover 30, a side surface 51*r* further on the surface 50*i* side than the one side 56*e* of the thin plate-like part 56 of the columnar section 51 and a surface 56r configuring the surface 56i of the one side 56e.

That is, the side surface 51r and the surface 56r exposed to the insert-through path 50r configure, in conjunction with the second surface 30t of the one side 30e, a surface that guides the one side 40r and the connection piece 41 of the chain member for left-right bending 40 forward and backward in the inserting direction S.

The insert-through path 50l, which is the second insert-through path through which the other side 40l and the connection piece 42 of the chain member for left-right bending 40 are inserted, is formed in the chain separator 50 by, in conjunction with the second surface 30t of the other side 30f of the first chain cover 30, a side surface 51l further on the surface 50i side than the other side 56f of the thin plate-like part 56 of the columnar section 51 and a surface 56l configuring the surface 56i of the other side 56f.

That is, the side surface 51l and the surface 56l exposed to the insert-through path 50l configure, in conjunction with the second surface 30t of the other side 30f, a surface that guides the other side 40l and the connection piece 42 of the chain member for left-right bending 40 forward and backward in the inserting direction S.

Further, the insert-through path 50u, which is the first insert-through path through which the one side 60u and the connection piece 61 of the chain member for up-down bending 60 are inserted, is formed in the chain separator 50 by, in conjunction with the second surface 70i of the one side 70e of the second chain cover 70, a side surface 51u further on the surface 50t side than the one side 56e of the thin plate-like part 56 of the columnar section 51 and a surface 56u configuring the surface 56t of the one side 56e.

That is, the side surface 51u and the surface 56u exposed to the insert-through path 50u configure, in conjunction with the second surface 70i of the one side 70e, a surface that guides the one side 60u and the connection piece 61 of the chain member for up-down bending 60 forward and backward in the inserting direction S.

The insert-through path 50d, which is the second insert-through path through which the other side 60d and the connection piece 62 of the chain member for up-down bending 60 are inserted, is formed in the chain separator 50 by, in conjunction with the second surface 70i of the other side 70f of the second chain cover 70, a side surface 51d further on the surface 50t side than the other side 56f of the thin plate-like part 56 of the columnar section 51 and a surface 56d configuring the surface 56t of the other side 56f.

That is, the side surface 51d and the surface 56d exposed to the insert-through path 50d configure, in conjunction with the second surface 70i of the other side 70f, a surface that guides the other side 60d and the connection piece 62 of the chain member for up-down bending 60 forward and backward in the inserting direction S.

Note that the insert-through path 50r and the insert-through path 50u are located to be superimposed apart from each other in the superimposing direction H across the one side 56e of the thin plate-like part 56. Therefore, the one side 40r and the connection piece 41 of the chain member for left-right bending 40 and the one side 60u and the connection piece 61 of the chain member for up-down bending 60 are located to be superimposed apart from each other in the superimposing direction H across the one side 56e of the thin plate-like part 56.

The insert-through path 50l and the insert-through path 50d are located to be superimposed apart from each other in the superimposing direction H across the other side 56f of the thin plate-like part 56. Therefore, the other side 40l and the connection piece 42 of the chain member for left-right bending 40 and the other side 60d and the connection piece 62 of the chain member for up-down bending 60 are located to be superimposed apart from each other in the superimposing direction H across the other side 56f of the thin plate-like part 56.

Further, the insert-through path 50r and the insert-through path 50l are located to be superimposed apart from each other in the width direction B across the columnar section 51. Similarly, the insert-through path 50u and the insert-through path 50d are located to be superimposed apart from each other in the width direction B across the columnar section 51.

At an end portion on the outer side in the width direction B of the surface 56r of the one side 56e of the thin plate-like part 56, the rib 55r, which is the fifth projecting section, is formed. The rib 55r guides, in conjunction with the rib 35, the one side 40r and the connection piece 41 of the chain member for left-right bending 40 not to come off to the outer side in the width direction B from the surface 56r, that is, guides the one side 40r and the connection piece 41 of the chain member for left-right bending 40 forward and backward in the inserting direction S not to come off the insert-through path 50r.

Further, at an end portion on the outer side in the width direction B of the surface 56l of the other side 56f of the thin plate-like part 56, the rib 55l, which is the fifth projecting section, is formed. The rib 55l guides, in conjunction with the rib 35, the other side 40l and the connection piece 42 of the chain member for left-right bending 40 not to come off to the outer side in the width direction B from the surface 56l, that is, guides the other side 40l and the connection piece 42 of the chain member for left-right bending 40 forward and backward in the inserting direction S not to come off the insert-through path 50l.

At an end portion on an outer side in the width direction B of the surface 56u of the one side 56e of the thin plate-like part 56, the rib 55u, which is the eighth projecting section, is formed. The rib 55u guides, in conjunction with the rib 75, the one side 60u and the connection piece 61 of the chain member for up-down bending 60 not to come off to the outer side in the width direction B from the surface 56u, that is, guides the one side 60u and the connection piece 61 of the chain member for up-down bending 60 forward and backward in the inserting direction S not to come off the insert-through path 50u.

Further, at an end portion on the outer side in the width direction B of the surface 56d of the other side 56f of the thin plate-like part 56, the rib 55d, which is the eighth projecting section, is formed. The rib 55d guides, in conjunction with the rib 75, the other side 60d and the connection piece 62 of the chain member for up-down bending 60 not to come off to the outer side in the width direction B from the surface 56d, that is, guides the other side 60d and the connection piece 62 of the chain member for up-down bending 60 forward and backward in the inserting direction S not to come off the insert-through path 50d.

Note that, when the frame body 20, the first chain cover 30, the sprocket 45, the chain member for left-right bending 40, the chain separator 50, the sprocket 65, the chain member for up-down bending 60, and the second chain cover 70 are assembled, first, the positioning holes 32 of the first chain cover 30 are fit in the positioning protrusions 22 of the frame body 20. The plurality of projecting sections 31 formed on the first surface 30i of the first chain cover 30 are fit in the plurality of holes 21 of the frame body 20. Consequently, in a state in which the first chain cover 30 is positioned in the frame body 20, the first surface 30$i$ of the first chain cover 30 is set in contact with the surface 20$t$ of the frame body 20.

Thereafter, after the sprocket 45 is engaged in the holding hole 38 of the first chain cover 30, an intermediate position of the chain member for left-right bending 40 is wound around the winding section 45$m$ of the sprocket 45, whereby the chain member for left-right bending 40 is placed on the second surface 30$t$ of the first chain cover 30.

At this point, the one side 40$r$ and the connection piece 41 of the chain member for left-right bending 40 are placed on the second surface 30$t$ of the one side 30$e$ of the first chain cover 30. The other side 40$l$ and the connection piece 42 are placed on the second surface 30$t$ of the other side 30$f$.

In this state, the one side 40$r$, the connection piece 41, the other side 40$l$, and the connection piece 42 are prevented from coming off the second surface 30$t$ by the ribs 34 and 35.

Thereafter, the locking sections 50$w$ provided at the distal end of the chain separator 50 are locked to the respective locking grooves 25$t$ of the two supporting members 25$e$ and 25$f$ standing from the second surface 30$t$ of the first chain cover 30. The columnar section 51 of the chain separator 50 is set in contact with the surface 20$t$ of the frame body 20 via the slit 39 of the first chain cover 30. Further, the chain separator 50 is fixed to the surface 20$t$ of the frame body 20 such that the one side 40$r$ and the connection piece 41 and the other side 40$l$ and the connection piece 42 of the chain member for left-right bending 40 are inserted through the respective insert-through paths 50$r$ and 50$l$ and the sprocket 45 is held in the holding hole 58.

Subsequently, after an intermediate position of the chain member for up-down bending 60 is wound around the winding section 65$m$ of the sprocket 65, the sprocket 65 is engaged in the holding hole 58 of the chain separator 50, whereby the chain member for up-down bending 60 is placed on the surface 56$t$ of the thin plate-like part 56 of the chain separator 50.

At this point, the one side 60$u$ and the connection piece 61 of the chain member for up-down bending 60 are placed on the surface 56$u$ configuring the surface 56$t$ of the one side 56$e$ of the thin plate-like part 56. The other side 60$d$ and the connection piece 62 are placed on the surface 56$d$ configuring the surface 56$t$ of the other side 56$f$ of the thin plate-like part 56.

In this state, the one side 60$u$, the connection piece 61, the other side 60$d$, and the connection piece 62 are prevented from coming off the surface 56$t$ by the ribs 55$u$ and 55$d$.

Finally, the positioning holes 72 of the second chain cover 70 are fit in the positioning protrusions 52 of the chain separator 50. The sprocket 65 is engaged in the holding hole 78 of the second chain cover 70. The second surface 70$i$ of the second chain cover 70 is set in contact with the surface 50$t$ of the chain separator 50 in a state in which the second chain cover 70 is positioned with respect to the chain separator 50. As a result, the one side 60$u$ and the connection piece 61 and the other side 60$d$ and the connection piece 62 of the chain member for up-down bending 60 are inserted through the respective insert-through paths 50$u$ and 50$d$.

In this way, in the present embodiment, the first chain cover 30 is explained as being sandwiched and located between the chain separator 50 and the frame body 20.

The plurality of holes 21 are explained as being formed in the frame body 20. The plurality of projecting sections 31 formed on the first surface 30$i$ of the first chain cover 30 are explained as being fit in the plurality of holes 21 of the frame body 20.

Further, the chain member for left-right bending 40 is explained as sliding with respect to the second surface 30$t$ of the first chain cover 30.

Consequently, since the plurality of holes 21 are formed in the frame body 20, it is possible to realize a reduction in the weight of the frame body 20.

Since the plurality of projecting sections 31 are fit in the plurality of holes 21, the plurality of holes 21 are closed by the plurality of projecting sections 31. Therefore, when various members are assembled in the operation section 3, the various members can be prevented from being caught by the plurality of holes 21. Therefore, assemblability of the various members in the operation section 3 is improved.

The chain member for left-right bending 40 slides with respect to the second surface 30$t$ of the first chain cover 30. Therefore, during the movement, the chain member for left-right bending 40 is not caught by the plurality of holes 21 of the frame body 20.

Further, in the present embodiment, the guide projecting section 36 fitting in the plurality of holes 21 is explained as being provided in the projecting section 31.

Consequently, the guide projecting section 36 can define a traveling direction of the various members in the operation section 3 and prevent the various members from being caught by the level difference of the inner wall in the operation section main body 3$h$ and prevent buckling of the various members. Therefore, assemblability of the various members in the operation section 3 is improved.

In the present embodiment, the ribs 34 and 35 are explained as being formed along the inserting direction S at the end portion in the width direction B on the second surfaces 30$t$ of the one side 30$e$ and the other side 30$f$ of the first chain cover 30.

Consequently, the chain member for left-right bending 40 and the connection pieces 41 and 42 are prevented from coming off the second surfaces 30$t$ of the one side 30$e$ and the other side 30$f$ of the first chain cover 30 by the ribs 34 and 35.

In the present embodiment, the projecting section for alignment 33 is explained as being formed in the front and the vicinity of the holding hole 38 on the second surface 30$t$ of the first chain cover 30.

Consequently, the one side 40$r$ and the other side 40$l$ can be prevented from interfering with each other because of loosening of one of the one side 40$r$ and the other side 40$l$ of the chain member for left-right bending 40 by the projecting section for alignment 33.

Further, in the present embodiment, the first chain cover 30 and the second chain cover 70 are explained as having the same shape.

Consequently, since components can be used in common, it is possible to reduce manufacturing costs.

From the above, it is possible to provide the bending operation device 100 and the endoscope 1 including a configuration that achieves a reduction in weight of the operation section 3, facilitates assembly work of various members in the operation section 3, and enables stable movement of a long member.

Note that, in the present embodiment explained above, the plurality of projecting sections 31 formed on the first surface 30$i$ of the first chain cover 30 are explained as being fit in the plurality of holes 21 of the frame body 20.

The present invention is not limited to this. Naturally, a plurality of projecting sections formed on the surface 50$i$ of the chain separator 50 may be fit in the plurality of holes 21 to thereby close the plurality of holes 21. That is, naturally, the first chain cover 30 may be integrally formed in the chain separator 50.

In the present embodiment, the configuration in which the four insert-through paths 50r, 50l, 50u, and 50d of the long member are formed in the chain separator 50 is explained as the example. The present invention is not limited to this. When the bending section 2w bends only in two directions, only two insert-through paths of the long member may be formed in the chain separator 50.

Further, in the present embodiment, the endoscope 1 is explained as the example of the insertion device. However, the present invention is not limited to this and is also applicable to other insertion devices including a bending section and other moving sections in an insertion section. That is, the operation mechanism of the insertion device in the present embodiment is also applicable to an operation mechanism of an insertion device other than the endoscope.

Note that, in the present embodiment explained above, the chain separator 50 and the chain covers 30 and 70 are explained as being formed from resin. However, the present invention is not limited to this. Only the chain separator 50 may be formed from resin.

Figure 12:
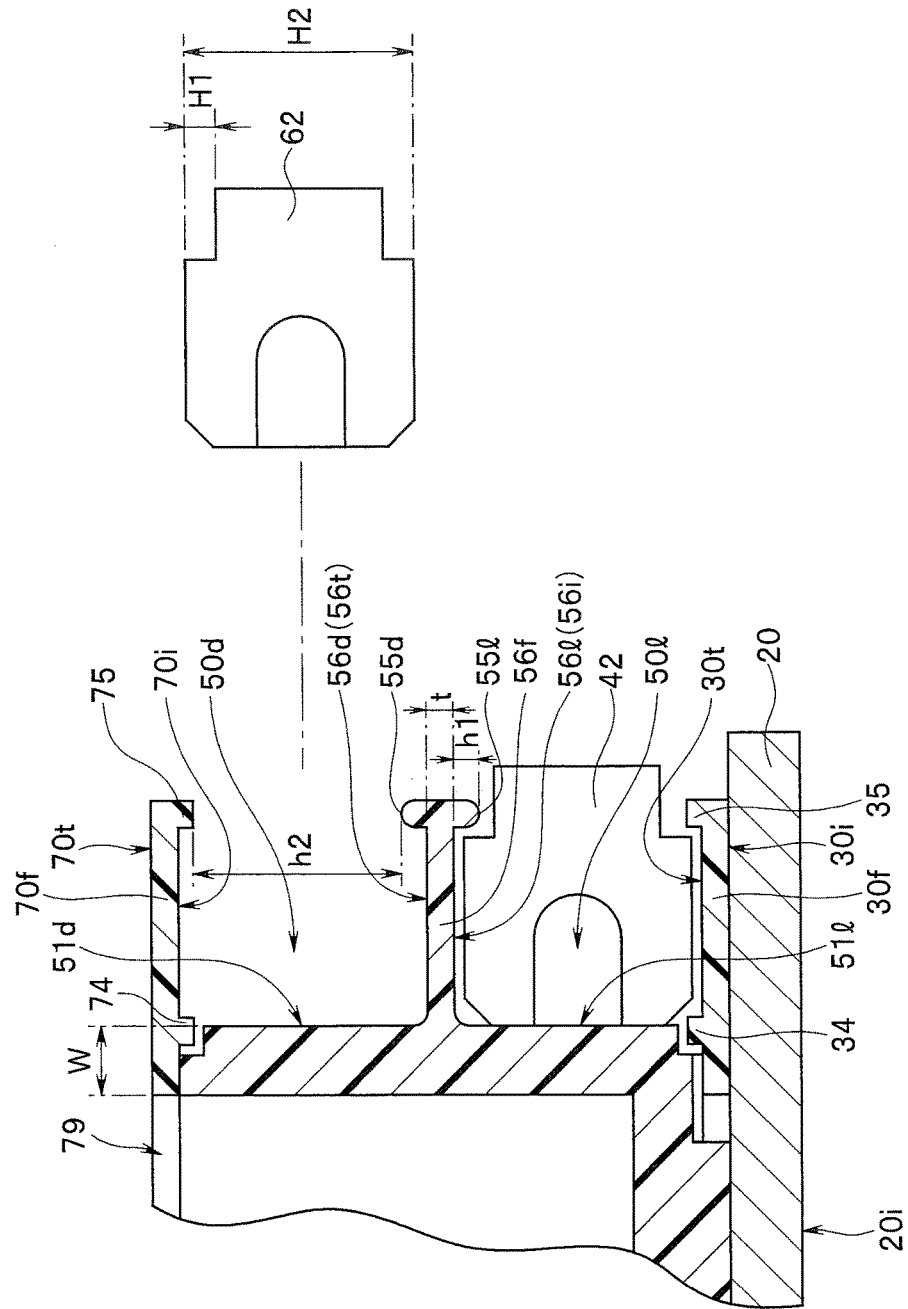
FIG. 12 is a partial sectional view of the chain separator showing a state in which a second connection piece is removed from an insert-through path in the chain separator shown in FIG. 7.
Figure 13:
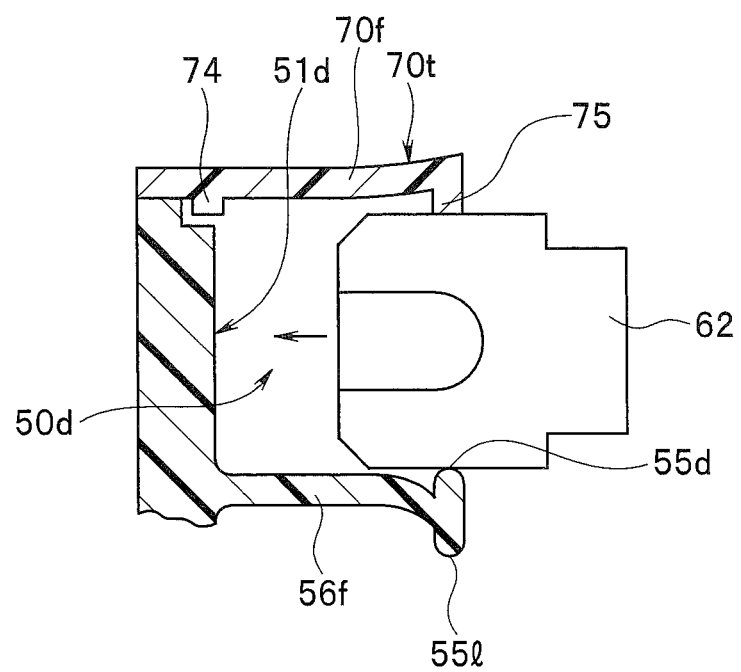
FIG. 13 is a partial sectional view showing a state in which the second connection piece shown in FIG. 12 is inserted into the insert-through path.
Figure 14:
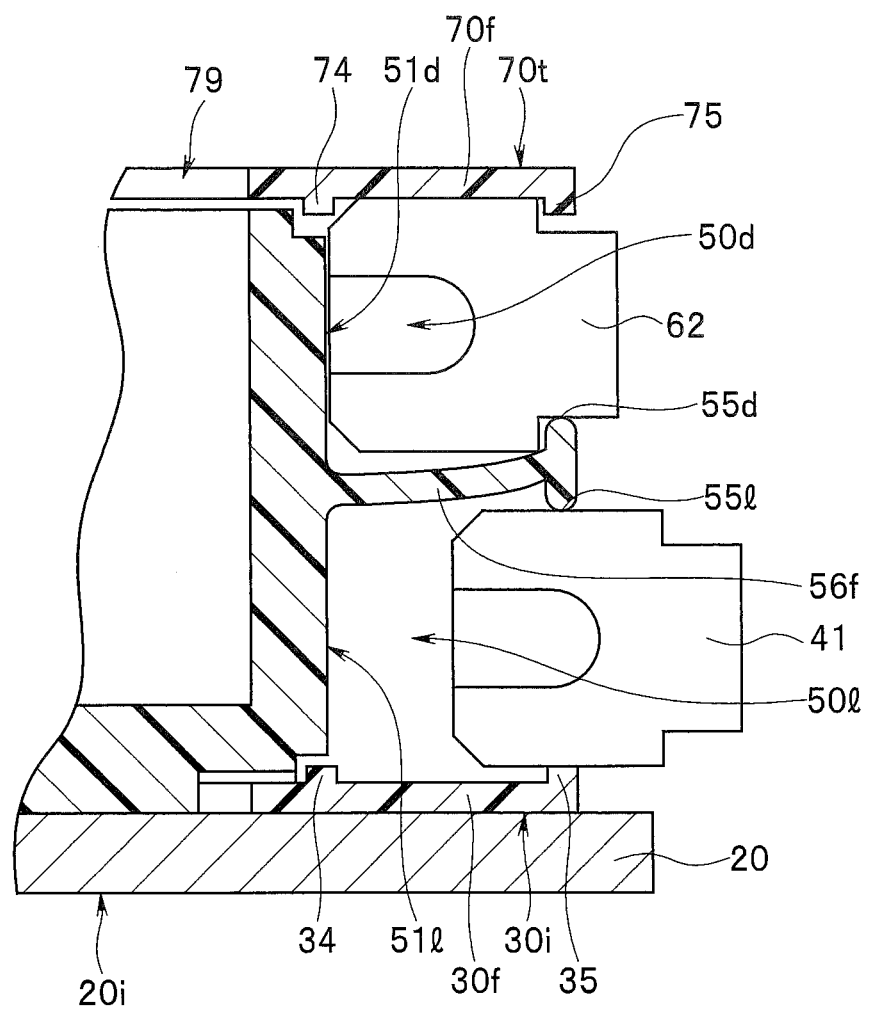
FIG. 14 is a partial sectional view showing a state in which the second connection piece is pushed up when the first connection piece is inserted into the insert-through path shown in FIG. 12.

Note that other modifications are explained below with reference to FIG. 12 to FIG. 14. FIG. 12 is a partial sectional view of the chain separator showing a state in which the second connection piece is removed from the insert-through path in the chain separator shown in FIG. 7. FIG. 13 is a partial sectional view showing a state in which the second connection piece shown in FIG. 12 is inserted into the insert-through path. FIG. 14 is a partial sectional view showing a state in which the second connection piece is pushed up when the first connection piece is inserted into the insert-through path shown in FIG. 12.

Incidentally, as explained above, in the assembly of the operation section 3, it is likely that the chain member for left-right bending 40 and the chain member for up-down bending 60 come off the chain separator 50. This is undesirable because assembly efficiency is deteriorated.

After the assembly of the operation section 3, in assembly of other parts and at the time of transportation during the assembly, it is also likely that the first connection pieces 41 and 61 and the second connection pieces 42 and 62 unintentionally come off the chain separator 50.

When the first connection pieces 41 and 61 and the second connection pieces 42 and 62 come off the chain separator 50, it is likely that the chain member for left-right bending 40 and the chain member for up-down bending 60 spread to an unintended part and are caught by parts other than the chain separator 50 of the operation section 3. The parts other than the chain separator 50 are sometimes defiled.

Therefore, it is also conceivable to adopt means for taking measures for provisionally pressing the first connection pieces 41 and 61 and the second connection pieces 42 and 62 using a tape or the like in order to restrict the come-off of the first connection pieces 41 and 61 and the second connection pieces 42 and 62. However, costs increase. Besides, there is also a problem that remains of an adhesive after peeling of the tape has to be treated.

In particular, the tape or the like affects slidability of the first connection pieces 41 and 61 and the second connection pieces 42 and 62 in the chain separator 50 if an adhesive member is left remained in the chain separator 50.

When the insertion section 2 and the operation section 3 are assembled, it is necessary to couple the first wires 90r and 90u and the second wires 90d and 90l, which control the bending section 2w of the insertion section 2, and the first connection pieces 41 and 61 and the second connection pieces 42 and 62.

Further, in general, specifications of the insertion section 2 are various depending on a type of the endoscope 1. However, the operation section 3 is structured to be capable of being used generally in common in a plurality of types of endoscopes.

Therefore, as explained above, it is desired to prevent the first connection pieces 41 and 61 and the second connection pieces 42 and 62 from unintentionally coming off the chain separator 50. However, for example, in assembly of the insertion section 2 and the operation section 3, it is desired to structure the first connection pieces 41 and 61 and the second connection pieces 42 and 62 to be easily drawn out from the chain separator 50 and easily housed.

Therefore, as shown in FIG. 12, the chain separator 50 is desirably configured from an elastic body entirely or partially in the thin plate-like parts 56e and 56f and the ribs 55r, 55u, 55l, and 55d. The second chain cover 70 is also desirably configured from an elastic body.

More specifically, height h1 of the ribs 55r, 55u, 55l, and 55d is formed smaller than height H1 of hook sections of the first connection pieces 41 and 61 and the second connection pieces 42 and 62 (h1<H1). Outlet width h2 of the insert-through paths 50r, 50u, 50l, and 50d is formed smaller than height H2 of the first connection pieces 41 and 61 and the second connection pieces 42 and 62 (h2<H2).

Further, thickness t of the thin plate-like parts 56e and 56f is formed smaller than width W of the columnar section 51. Outer circumferences of the respective ribs 55r, 55u, 55l, and 55d are rounded at corners or chamfered in order to prevent the first connection pieces 41 and 61 and the second connection pieces 42 and 62 from being caught.

In this way, the thin plate-like parts 56e and 56f, the ribs 55r, 55u, 55l, and 55d, the first chain cover 30, and the second chain cover 70 are formed from the elastic bodies. Therefore, for example, as shown in FIG. 13, when the second connection piece 62 is inserted into and pulled out from the insert-through path 50d of the chain separator 50, the thin plate-like part 56f is bent and deformed and the other side 70f of the second chain cover 70 also rises to be bent and deformed.

Further, for example, as shown in FIG. 14, when the second connection piece 42 is inserted into and pulled out from the insert-through path 50l of the chain separator 50, the other side 30f of the first chain cover 30 is not bent and deformed and the thin plate-like part 56f is pushed by the second connection piece 42 and bent and deformed.

Note that, at this point, as shown in FIG. 14, when the second connection piece 62 is housed in the insert-through path 50d, the second connection piece 62 may be lifted by being pressed by the thin plate-like part 56f and the other side 30f may also, for example, rise to be bent and deformed.

With such configurations shown in FIG. 12 to FIG. 14, even if the operation section 3 being assembled is tilted or slightly vibrated, the first connection pieces 41 and 61 and the second connection pieces 42 and 62 do not come off the insert-through paths 50r to 50d.

When the first connection pieces 41 and 61 and the second connection pieces 42 and 62 are inserted into and pulled out from the respective insert-through paths 50r to 50d, if the chain separator 50 is slightly bent or deformed, the first connection pieces 41 and 61 and the second connection pieces 42 and 62 are easily inserted into and pulled out from the respective insert-through paths 50r to 50d.

What is claimed is:

1. An operation mechanism for an insertion device, the operation mechanism comprising:
   a moving section movably provided in an insertion section inserted into a subject/object;
   an operation section concatenated to the insertion section in order to operate the moving section;
   a tabular frame body fixed in the operation section, the tabular body including a plurality of holes and configured to position built-in components of the operation section;
   an elongated member movable along the frame body according to the operation of the operation section; and
   a first tabular member provided between the frame body and the elongated member in the operation section, the first tabular body including a surface that guides the elongated member;
   wherein the first tabular member includes a plurality of first projecting sections projecting from a surface opposed to the surface that guides the elongated member to a frame body side, and
   the plurality of first projecting sections are disposed in the plurality of holes.

2. The operation mechanism for the insertion device according to claim 1, wherein a thickness of the plurality of first projecting sections in a superimposing direction of the frame body and the first annular member is smaller than a thickness of the frame body in the superimposing direction.

3. The operation mechanism for the insertion device according to claim 2, wherein the plurality of first projecting sections each has a different thickness in the superimposing direction.

4. The operation mechanism for the insertion device according to claim 1, wherein
   a thickness of the plurality of first projecting sections is formed same as a thickness of the frame body in the superimposing direction of the frame body and the first tabular member, and
   in a state in which the plurality of first projecting sections are fit in the plurality of holes, top surfaces of the respective first projecting sections are flush with a surface of the frame body on an opposite side of a surface of the frame body in contact with the opposed surface of the first tabular member.

5. The operation mechanism for the insertion device according to claim 1, wherein the plurality of first projecting sections each has a different shape.

6. The operation mechanism for the insertion device according to claim 1, wherein a shape of the plurality of first projecting sections is formed in a shape same as a shape of the plurality of holes.

7. The operation mechanism for the insertion device according to claim 1, wherein the plurality of first projecting sections are formed in a shape in which only a circumferential edge portion projects to the frame body side from the opposed surface of the first tabular member and a surface between the circumferential edge portion and the opposed surface is an inclined surface.

8. The operation mechanism for the insertion device according to claim 1, wherein a second projecting section fitting in the plurality of holes and configured to guide disposition of a member provided in the operation section is provided in at least one of the opposed surface of the first tabular member and the plurality of first projecting sections.

9. The operation mechanism for the insertion device according to claim 1, wherein the frame body is made of metal and the first tabular member is made of resin.

10. The operation mechanism for the insertion device according to claim 1, further comprising a projecting section provided to project along a direction in which the elongated member moves on a surface that guides the elongated member and configured to guide the elongated member not to come off the surface that guides the elongated member.

11. The operation mechanism for the insertion device according to claim 10, further comprising a guide member fixed to the frame body in the operation section, the guide member including a second tabular portion including the surface that guides the elongated member, wherein
   the projecting section is provided on the surface that guides the elongated member in the second tabular portion.

12. The operation mechanism for the insertion device according to claim 11, wherein
   the moving section is a bending section configured to bend the insertion section in an up-down direction and a left-right direction,
   the elongated member includes a first elongated member configured to bend the moving section in the up-down direction according to the operation of the operation section and a second elongated member configured to bend the moving section in the left-right direction according to the operation of the operation section,
   the second tabular portion includes a first surface that guides the first elongated member and a second surface that guides the second elongated member, and
   the projecting section includes at least one of a portion projecting from the first surface and a portion projecting from the second surface.

13. The operation mechanism for the insertion device according to claim 10, wherein
   a turning shaft and a turning body fixed to the turning shaft are provided in the operation section, and the elongated member is wound around the turning body,
   the elongated member is connected to, via a connection piece, another elongated member connected to the moving section, and
   the projecting section is provided, to prevent the connection piece from coming off, in a range in which the connection piece moves.

14. An insertion device comprising:
   an operation mechanism comprising:
      a moving section movably provided in an insertion section inserted into a subject/object;
      an operation section concatenated to the insertion section in order to operate the moving section;
      a tabular frame body fixed in the operation section, the tabular body including a plurality of holes and configured to position built-in components of the operation section;
      an elongated member movable along the frame body according to the operation of the operation section; and
      a first tabular member provided between the frame body and the elongated member in the operation section, the first tabular body including a surface that guides the elongated member;
      wherein the first tabular member includes a plurality of first projecting sections projecting from a surface opposed to the surface that guides the elongated member to a frame body side, and
      the plurality of first projecting sections are disposed in the plurality of holes.

* * * * *